US009555059B2

(12) United States Patent
Gorselink et al.

(10) Patent No.: US 9,555,059 B2
(45) Date of Patent: *Jan. 31, 2017

(54) USE OF DIETARY FIBRES AGAINST MUSCLE WASTING

(75) Inventors: Marchel Gorselink, Velp (NL); Adrianus Lambertus Bertholdus van Helvoort, Wageningen (NL); Robert Johan Joseph Hageman, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 420 days.

This patent is subject to a terminal disclaimer.

(21) Appl. No.: 13/411,227

(22) Filed: Mar. 2, 2012

(65) Prior Publication Data

US 2012/0165243 A1 Jun. 28, 2012

Related U.S. Application Data

(63) Continuation of application No. 12/097,667, filed as application No. PCT/NL2006/050320 on Dec. 18, 2006, now Pat. No. 8,143,235.

(30) Foreign Application Priority Data

Dec. 16, 2005 (EP) ..................................... 05112336

(51) Int. Cl.

| | | |
|---|---|---|
| *A61K 31/702* | (2006.01) | |
| *C07H 3/06* | (2006.01) | |
| *C08B 37/00* | (2006.01) | |
| *A61K 35/20* | (2006.01) | |
| *A61K 31/729* | (2006.01) | |
| *A61K 31/731* | (2006.01) | |
| *A61K 31/736* | (2006.01) | |
| *A61K 31/715* | (2006.01) | |
| *A61K 31/733* | (2006.01) | |

(52) U.S. Cl.
CPC ............... *A61K 35/20* (2013.01); *A23L 33/21* (2016.08); *A23L 33/40* (2016.08); *A61K 31/702* (2013.01); *A61K 31/715* (2013.01); *A61K 31/729* (2013.01); *A61K 31/731* (2013.01); *A61K 31/733* (2013.01); *A61K 31/736* (2013.01); *C07H 3/06* (2013.01); *A23V 2002/00* (2013.01)

(58) Field of Classification Search
CPC ................................ A61K 31/707; C07H 3/06
See application file for complete search history.

(56) References Cited

U.S. PATENT DOCUMENTS

| | | | |
|---|---|---|---|
| 5,444,054 A | 8/1995 | Garleb et al. | |
| 5,641,531 A | 6/1997 | Liebrecht et al. | |
| 5,776,524 A | 7/1998 | Reinhart | |
| 5,817,695 A | 10/1998 | Pellico | |
| 6,387,883 B1 | 5/2002 | Abbruzzese et al. | |
| 6,420,342 B1 | 7/2002 | Hageman et al. | |
| 6,887,850 B2 | 5/2005 | Fuchs et al. | |
| 2002/0028196 A1 | 3/2002 | Percival et al. | |
| 2005/0153019 A1 | 7/2005 | Fuchs et al. | |
| 2008/0171720 A1 | 7/2008 | Garssen et al. | |

FOREIGN PATENT DOCUMENTS

| | | | |
|---|---|---|---|
| EP | 0 721 742 B1 | 6/2002 | |
| EP | 1 105 002 B1 | 7/2002 | |
| WO | WO-97/39749 A2 | 10/1997 | |
| WO | WO-02/15720 A2 | 2/2002 | |
| WO | WO-02/26242 A2 | 4/2002 | |
| WO | WO-2004/026294 A1 | 4/2004 | |
| WO | WO 2005/039597 | * 5/2005 | ............. A61K 31/70 |
| WO | WO-2005/039597 A2 | 5/2005 | |
| WO | WO-2009/157759 A1 | 12/2009 | |
| WO | WO-2009/157767 A1 | 12/2009 | |

OTHER PUBLICATIONS

Edström et al., "Sarcopenia is not due to lack of regenerative drive in senescent skeletal muscle" Aging Cell, 2005, 4(2):65-77.
Gennaro et al., "Studies on the physicochemical properties of inulin and inulin oligomers" Food Chem, 2000,68(2):179-183.
Hsu et al., "Xylooligosaccharides and Fructooligosaccharides affect the intestinal microbiota and precancerouse colonic lesion development in rats" J Nutr, 2004, 134(6):1523-1528.
International Search Report for PCT/NL2006/050320, dated Apr. 25, 2007 (3 pages).
McDonough et al. "Whey Protein Concentrate as Milk Extender" J Dairy Sci, 1976, 59(1):34-40.
Muscaritoli et al., "Prevention and treatment of cancer cachexia: New insights into an old problem" Eur J Cancer, 2006, 42(1):31-41.
Pool-Zobel, "Inulin-type fructans and reduction in colon cancer risk: review of experimental and human data" Brit J Nutr, 2005, 93(S1):S73-S90.
Sharpstone, et al., "Gastrointestinal manifestations of HIV infection", The Lancet (1996) vol. 348, pp. 379-383.
Tanaka et al., "Experimental Cancer Cachexia Induced by Transplantable Colon 26 Adenocarcinoma in Mice" Cancer Res, 1990, 50(8):2290-2295.
Tang et al., "Effect of dietary supplementation of chitosan and galacto-mannan-oligosaccharide on serum parameters and the insulin-like growth factor-I mRNA expressin in early-weaned piglets" Domest Anim Endocrin, 2005, 28(4):430-441.
Taper et al., "Influence of Inulin and Oligofructose on Breast Cancer and Tumor Growth" J Nutr, 1999, 129(7):1488-1491.
US Office Action Dtd Mar. 1, 2011.
US Office Action Dtd Jul. 12, 2011.

(Continued)

*Primary Examiner* — Eric Olson
(74) *Attorney, Agent, or Firm* — Foley & Lardner LLP; Sunit Talapatra

(57) ABSTRACT

A composition nutritional containing dietary fibers is useful for the treatment of muscle wasting, if the dietary fiber comprise at least 30 wt. % of galacto-oligosaccharides or other oligosaccharides having mainly anhydropyranose units, and having a chain length of 3-10 units. The composition may further contain other oligo- or polysaccharides, especially polysaccharides having a majority of anhydrofuranose units.

17 Claims, No Drawings

(56) References Cited

OTHER PUBLICATIONS

Wijnands et al., "A comparison of the effects of dietary cellulose and fermentable galacto-oligosaccharide, in a rat model of colorectal carcinogenesis:fermentable fiber confers greater protection than non-fermentable fiber in both high and low fat backgrounds" Carcinogenesis, 1999, 20(4):651-656.

Wijands et al., "Effect of dietary galacto-oligosaccharides on azoxymethane-induced aberrant crypt foci and colorectal cancer in Fischer 344 rats" Carcinogenesis, 2001, 22(1):127-132.

Burns, et al. "Antigenotoxicity of probiotics and prebiotics on faecal water-induced DNA damage in human colon adenocarcinoma cells", Mutation Research, 2004, vol. 551, pp. 233-243.

Cummings, et al. "Review—A new look at dietary carbohydrate: chemistry, physiology and health", European Journal of Clinical Nutrition, 1997, vol. 51, pp. 417-423.

Faber, et al. "Beneficial immune modulatory effects of a specific nutritional combination in a murine model for cancer cachexia", British Journal of Cancer, 2008, vol. 99, pp. 2029-2036.

Gordon, et al. "Review—Cancer cachexia", Q J Med, 2005, vol. 98, pp. 779-788.

Hodin, "Maintaining Gut Homeostasis: The Butyrate-NF-kB Connection", Gastroenterology, Apr. 2000, vol. 118, No. 4, pp. 798-801.

McKinnell, et al. "Molecular Mechanisms of Muscle Atrophy", Cell, Dec. 29, 2004, vol. 119, pp. 907-910.

* cited by examiner

USE OF DIETARY FIBRES AGAINST MUSCLE WASTING

CROSS REFERENCE TO RELATED APPLICATIONS

This application is a continuation of U.S. patent application Ser. No. 12/097,667, filed Nov. 14, 2008, which is a national stage of PCT/NL2006/050320, filed Dec. 18, 2006, which claims priority to European Patent Application No. 05112336.2, filed Dec. 16, 2005. The entire contents of the aforementioned are incorporated herein by reference.

TECHNICAL FIELD OF THE INVENTION

The present invention relates to the use of a nutritional or pharmaceutical composition comprising non-digestible oligosaccharides for the treatment or reduction of the incidence of muscle wasting.

BACKGROUND OF THE INVENTION

Severe weight loss and in particular muscle wasting is a serious phenomenon that occurs on a broad scale in patients suffering from diseases, disorders and trauma. Muscle wasting (abbreviated as MW) in chronic disease is defined as an involuntary loss of body weight of more than 5% within one month. If loss of lean body mass (abbreviated as LBM) occurs at a more gradual rate but during a longer period, the inventors refer to chronic muscle wasting (abbreviated as CMW), in particular if more than 10% of body weight is lost in a period of 6 months. MW is typically observed during recovery of trauma or surgery. CMW is typically observed in severe diseases such as cancer, AIDS, COPD, diabetes mellitus and heart failure. The rate of muscle wasting is associated with increased morbidity and mortality. The cause of muscle wasting as a result of a disease is thought to be multifactorial. Muscle wasting can also be caused by malnourishment, in particular protein-energy malnourishment. In particular the latter type of malnourishment can be treated or prevented by providing extra protein or energy as proposed in EP 0721742.

Sarcopenia (abbreviated as SP) is the involuntary decline in lean muscle mass, strength and function, which occurs with ageing. SP increases the risk of loss of functional capacity in the elderly, which is not necessarily related to disease.

Dietary fibres are frequently used to initiate weight loss. Dietary fibre lowers postprandial glucose levels in blood and has a satiating effect. Therefore, administration of substantial amounts of dietary fibre is not normally recommended in cases of malnutrition, weight loss and muscle wasting. Dietary fibre has also been included in clinical nutrition for influencing colonic flora and specific fibres or mixtures thereof have been claimed to decrease rate of systemic infections, e.g. in WO 02/26242, increase specific immune-related parameters, e.g. in EP-B 1105002, or decrease growth rate of selected tumours in animals, e.g. in Taper H., J Nutr., 129 (1999), 1488-1491.

Many types of dietary fibre have been used in the manufacture of nutritional products. Several of them strongly increase viscosity, others have a bad solubility or produce a sand-like feeling when present in the mouth. Thus, there is a need for nutritional products, which can be readily consumed by persons suffering from muscle wasting or chronic muscle wasting, and which combat or prevent muscle wasting without having the disadvantages of prior art products, such as a high viscosity of liquid drinks WO 2004/026294 discloses the use of a mixture of free essential amino acids including leucine for improving the effects of tumour-induced weight loss. The mixture can be combined with further components such as intact protein, ω-3 fatty acids and soluble fibre such as hydrolysed guar gum.

U.S. Pat. No. 6,387,883 teaches treatment of cachexia and anorexia by administration of ω-3 fatty acids, branched-chain amino acids, and further components possibly including dietary fibre.

US 2005/153019 is concerned with stimulating body protein synthesis by providing a composition containing whey protein, ω-3 fatty acids, carbohydrates, vitamins, etc. The composition may further contain prebiotic fibre, such as fructo-oligosaccharides, for promoting growth of bifidobacteria, but such compositions are not further illustrated.

U.S. Pat. No. 5,444,054 teaches a method of improving nutritional status in case of ulcerative colitis or colic inflammation, using a combination of the ω-3 fatty acids EPA and DHA, and indigestible carbohydrates, such as gum Arabic and fructo- and xylo-oligosaccharides.

DESCRIPTION OF THE INVENTION

It was surprisingly found that a dietary fibre comprising at least 30 wt. % of non-digestible oligosaccharides and a nutritional or pharmaceutical product containing such fibre fulfil this need. This is in contrast to the prior art, which frequently uses fibres to initiate weight loss. The non-digestible soluble oligosaccharides to be used according to the invention have a chain length of 3-10 anhydromonose units.

In a preferred embodiment, the anhydromonose units of the non-digestible oligo-saccharides have a majority of anhydropyranose units. These anhydropyranose units have a six-membered ring structure and comprise the anhydro forms of aldoses such as galactose, mannose, xylose, as well as their deoxy forms (such as fucose and rhamnose), their acid forms such as galacturonates and glucuronates, and their amino forms and N-acylamino forms (such as galactosamine), as well as their higher homologues (such as neuraminic acid and other sialic acids). They may also comprise anhydroglucose units and their derivatives, as long as the oligosaccharides remain essentially indigestible. Therefore, the oligosaccharides do not contain more than 2 or preferably less than two α-1,4-linked anhydroglucose units. Also, a minority of other anhydromonose units, e.g. anhydroarabinose units, (whether in pyranoside or furanoside form), may be present in the oligosaccharides. The anhydromonose units may be connected to each other by α- or β-linkages between the first (anomeric) carbon atom of one anhydromonose with the $2^{nd}$, $3^{rd}$, $4^{th}$ (or $6^{th}$ in the case of hexoses) carbon atom of the neighbouring anhydromonose moiety by means of an oxygen atom, as has been described in the art for many indigestible carbohydrates.

The preferred oligosaccharides of this embodiment are galacto-, manno- and/or xylo-oligosaccharides. They can be homo-oligosaccharides or hetero-oligosaccharides containing galactose, mannose and/or xylose units, which may further contain 10 to 35% anhydroglucose and/or anhydroarabinose units, anhydrofucose, anhydroglycosamine and/or N-acetyl-anhydroglycosamine units, preferably in a terminal position. Though hetero-oligomers are effective, it is sometimes preferred from a cost-effective point of view to include homologous variants of the pyranose oligosaccharides. In this context oligosaccharides having only a single different monosaccharide unit at their terminal position, such as a glucose unit in galacto-oligosaccharides, are still considered to be homo-oligomers.

In another embodiment, the anhydromonose units of the non-digestible oligo-saccharides have a majority of anhydrofuranose units. These anhydrofuranose units have a five-membered ring structure and comprise the anhydro forms of aldoses or ketoses such as fructose or arabinose, as well as their deoxy forms, their amino forms and N-acylamino forms, as well as their higher homologues. They may also comprise anhydroglucose units and their derivatives, as long as the oligosaccharides remain essentially indigestible. Therefore, these oligosaccharides do not contain more than 2 or preferably less than two α-1,4-linked anhydroglucose units. Also, a minority of other anhydromonose units, whether in pyranoside or furanoside form, may be present in these oligosaccharides.

In a further, preferred embodiment of the invention, the oligosaccharides are composed of two classes, one having a majority of anhydropyranose units and one having a majority of anhydrofuranose units, each as defined above. In this embodiment, the dietary fibre contains at least 40 wt. %, preferably at least 50 wt. %, more preferably at least 60 wt. % of total non-digestible oligosaccharides, including 30-98 wt. %, preferably 50-96 wt. %, of oligosaccharides of the first class (pyranose-based) and 2-50 wt. %, preferably 4-30 wt. % of oligosaccharides of the second class (furanose-based). These weight percentages are based on the weight of the fibre composition. The weight ratio between the first class and the second class is preferably between 98:2 and 2:98, more preferably between 97:3 and 10:90, most preferably between 96:4 and 50:50.

The oligosaccharides to be used according to the invention can be obtained by methods well-known in the art. According to a first method, suitable polysaccharides can be hydrolysed selectively or at random by chemical (acid) or, preferably enzymatic, hydrolysis. For example guar gum, locust bean gum, carob or tara galactomannans can be subjected to a treatment with β-mannanase and/or α-galactosidase at pH 3-6 to produce a low-viscosity product, especially when part or all of the galactose is removed from the polymer through the action of α-galactosidase. As another example, galactans and arabinogalactans can be hydrolysed by the appropriate (endo-β-1,3-)galactans, optionally in combination with arabinosidases to remove the arabinose side chains, and xylans and arabinoxylans can be hydrolysed using (β-)xylanases, optionally together with arabinosidases and/or galacturonidases. By choosing the appropriate hydrolysis conditions, low-viscosity oligosaccharides having the required chain length can be obtained. In general, hetero-oligosaccharides such as galactosyl-oligomannans, arabinosyl-oligogalactans and arabinosyl-oligoxylans can be obtained upon endoglycolytic hydrolysis wherein the side chain is not removed, and largely homo-oligosaccharides can be obtained upon enzymatic removal of the side chains. In the case of hydrolysates of galactomannans such as guar gum, the amount of mannobiose, mannotriose and galacto-manno-oligo-saccharides is preferably more than 20%, preferably 40-100% of the oligosaccharides. As a further example, inulin can be used as such, or after chemical or enzymatic hydrolysis; such hydrolysis results in oligofructoses having a terminal glucose unit, and pure oligo-fructoses.

According to a second general method, (hetero)oligosaccharides can be manufactured by enzymatic transglycosylation of suitable substrates with one or more suitable enzymes or one or more micro organisms or yeasts equipped with these enzymes. Examples of suitable substrates are solutions of the mono- or di-hexoses, lactose or fibres or partial hydrolysates thereof, such as hydrolysates of guar gum.

In particular galacto-oligosaccharides (GOS) are very suitable for manufacturing effective nutritional or pharmaceutical compositions. Suitable galacto-oligosaccharides are commercially available and include oligosaccharides manufactured from lactose by means of a reaction with β-galactosidase. Preferably, these galacto-oligosaccharides comprise at least 67%, especially at least 80% by weight of oligosaccharides having a chain length of 3 up to 5 units, disregarding mono- and disaccharides such as lactose.

Effective doses of the soluble dietary fibre compositions are 0.1-20, preferably 0.6-10, more preferably 0.8-5 gram per dose for a person weighing 80 kg. For persons (including infants) having a different body weight the dose is proportionally lower. In terms of dosage per kg body weight, the preferred daily dosages are between 1.2 and 250 mg, preferably 7.5-130, more preferably 10-65 mg per kg per day.

Other parts of the soluble fibre fraction can include non-oligosaccharides, like soluble and fermentable and non-fermentable fibres, including polysaccharides from the furanose type. Examples are inulin, other fructo-polysaccharides (fructans), moderately hydrolysed pectin and other gums, like glucomannans (e.g. Konjac), galactomannans (e.g. guar), xanthan, and Arabic gum. These polysaccharides (having a chain length (DP) of more than 10 units) can be included up to 70 wt. % of the soluble fibre composition. However, it is preferred that the fibre composition contains at least 50%, more preferably at least 70%, up to e.g. 95 or even 98% or 100% of the oligosaccharides, especially the (galacto-, manno-, xylo-)oligosaccharides as defined above. The remainder may be constituted by one or more of the soluble polysaccharide fibres, especially of the fructan type. In addition to the soluble fibre fraction, non-soluble fibres can be incorporated in a fibre blend, like resistant starch, and non-soluble fermentable and non-fermentable fibres, such as cellulose. It is preferred that the non-soluble fibres represent less than 50 wt. % of the soluble fibre fraction, in particular between 5 and 25 wt. % thereof.

In specific embodiments, the soluble fibre composition may contain 2-50 wt. %, in particular 5-30 wt. % of fructans (DP≥3) and/or 2-35 wt. %, in particular 5-25 wt. % of other soluble polysaccharides, such as hydrolysed galactomannan (having more than 10 anhydromonose units).

Other components that beneficially can be included in the compositions are specific proteins, lipids, carbohydrates, and micro ingredients.

The compositions can be liquid, semi-solid or solid. In liquid solution, the inclusion of the oligosaccharides according to the invention results in non-viscous products, having a viscosity below 70, preferably 1-40, more preferably 2-30 MPa·s at 100 sec$^{-1}$ shear rate and 20° C., when included in effective amounts, which makes the solutions suitable for use as a tube feeding. In liquids the effective dose will be included in a serving size. For tube feeding this is assumed to be 2000 ml per day, given in two portions per day. When the liquid product is used as a supplement, e.g. in portions of 200 ml, the concentration can be calculated accordingly. Typically the concentration of effective oligosaccharides will be well below 15, e.g. 0.05-10, preferably 0.5-9, more preferably 1-8% weight/volume. When the product has a semi-solid form such as a pudding, or a solid form such as a bar, the product will be used as a supplement and has a serving size of 25-200 ml. The concentration will therefore be 0.1-20 g per 25-200 g product. On an energy basis, the content of the soluble fibre composition is preferably 0.5-10 g per 419 KJ (100 kcal), more preferably 1-4 g per 419 KJ (100 kcal).

The energy content of liquid compositions will typically be in the range of 2.5-16.8, preferably 5.0-16.8, more preferably 5.4-8.4, and most preferably 6.3-8.0 KJ/ml (0.6-4.0, preferably 1.2-4.0, more preferably 1.3-2.0 and most preferably 1.5-1.9 kcal/ml).

It is preferred that a nutritional composition according to the invention contains at least a protein fraction. The weight ratio between the fibre fraction and the protein fraction being preferably between 5:95 and 75:25, more preferably between 10:90 and 50:50.

The protein fraction should preferably comprise more than 45, preferably 48-70, more preferably 52-65 wt % essential amino acids, based on total amino acids. Essential amino acids are methionine, leucine, isoleucine, valine, phenylalanine, tryptophan, histidine, lysine and threonine. The amount of essential amino acids in liquid products will typically be more than 4.75 g, preferably 4.9-9.0, more preferably 5.1-7 g per 100 ml.

In particular it is preferred that the amount of leucine +isoleucine is more than 18.0 wt %, based on the total sum of amino acids, and more preferably 18.5-25 wt %. The amount of leucine is preferably more than 11.0, more preferably more than 11.4 wt %, most preferably 12.2-20 wt. %. The amount of branched chain amino acids will typically be more than 2.9, preferably 3.0-4.0, more preferably 3.0-3.4 g per 100 ml liquid product.

The energy contribution of the protein fraction is preferably 25-75, more preferably 26-60, most preferably 26-50 en % of the nutritional composition. The energy contribution of the intact protein fraction is preferably 17-40, more preferably 19-30, most preferably 20-29 en % of the nutritional composition. The protein fraction should preferably contain more than 10%, more preferably 20-60% of intact whey protein or peptide fragments thereof.

The lipid fraction should comprise long chain fatty acids of the omega-3 type. Long-chain means at least 18 C atoms. Particularly preferred are fatty acids having 20-26 carbon atoms and having 4 or more unsaturated bonds. The amount of the sum of long-chain polyunsaturated fatty acids should be more than 10 wt % of the sum of all fatty acids, preferably 15-50, more preferably 17-42, in particular 18-42 wt %. The weight ratio between ω-3 long-chain polyunsaturated fatty acids (LCP's), such as α-linoleic, stearidonic, timnodonic (EPA), clupanodonic (DPA), cervonic (DHA) and nisinic acid (THA), and the soluble fibre is preferably between 90:10 and 5:95, more preferably between 80:20 and 15:85. The combination of the long-chain polyunsaturated fatty acids and the soluble fibre and optional further components, can suitably be used as a food supplement. It is preferred that the soluble fibre comprises galacto-, manno- and/or xylo-oligosaccharides, especially galacto-oligosaccharides, at a level of e.g. at least 50% w/w of the soluble fibre. The energy contribution of the lipid fraction is preferably 15-45, more preferably 20-35 en % of the nutritional composition.

The carbohydrate fraction can comprise glucose, maltodextrins, starch and/or other sugars. In a preferred embodiment, the carbohydrate fraction comprises 5-50 wt % ribose, especially 8-25 wt. % of ribose in order to prevent muscle wasting. On the basis of the soluble fibre composition, ribose is preferably present in a weight ratio of between 9:1 and 1:9, more preferably 4:1 to 1:4. This combination can be used as a food supplement. It is preferred that such a supplement also comprises other digestible carbohydrates, in an amount of 1-19 parts per part of ribose. In a the nutritional composition also containing lipids and/or proteins, the energy contribution of the digestible carbohydrate fraction is preferably 15-55, more preferably 25-50 en % of composition.

It is further preferred that the carbohydrate fraction comprises lactose. If present the amount of lactose is more than 2, more preferably 3-40, most preferably 10-30 wt % of the digestible carbohydrate fraction. A useful carbohydrate composition can contain 3-40 wt. %, preferably 5-30 wt. %, of the soluble fibre composition as described above, and 3-40 wt. %, preferably 5-30 wt. %, of ribose and/or 5-40 wt. %, preferably 8-30 wt. % of lactose, and preferably 20-80 wt. %, more preferably 35-70 wt. % of other digestible carbohydrates.

Contrary to prior art knowledge it is important to include an available carbohydrate fraction which has a low glycemic index for achieving a decrease in the rate of muscle wasting or even an increase in body weight. The available carbohydrate fraction is defined to possess a low glycemic index (GI) its value is less than 70% of the value of glucose. The carbohydrate fraction should preferably contain more than 20% of these carbohydrates, more preferably 40-80 wt %. Low GI sugars include lactose, trehalose, isomalto-oligosaccharides (oligosaccharides having a predominant portion of α-1,6 glucose units).

It is also preferred to include a low amount of sweet sugars in order to increase food consumption of diseased persons. The amount of sugars having a sweetness less than 70% of that of sucrose should be more than 20 wt. % of the available carbohydrate fraction. In particular the amount is 25-60 wt. %. Low-sweetness sugars include palatinose (isomaltulose), maltodextrins DE 2-47, galactose, mannose, lactose and trehalose. Alternatively, the total proportion of low GI and/or low-sweetness sugars, selected from galactose, mannose, other glucose-containing disaccharides than sucrose and maltose (including lactose, trehalose and palatinose), and isomalto-oligosaccharides, is thus preferably 20-80 wt. %, more preferably 25-60%.

All minerals and micro ingredients that are required for proper feeding of human beings are typically included. Typically per daily dose 0.5-1.5× the recommended daily amounts are included, with the exception of folates, which are included in 1-4 times the recommended daily amounts (especially 300-1200 μg/day or 50-1000 μg, especially 60-600 μg per g soluble fibre).

EXAMPLE 1

Material & Methods

Male CD2F1 mice (BALB/c×DBA/2, Harlan, the Netherlands) were used and the C-26 adenocarcinoma cells were used to induce cachexia in the tumour-bearing groups (TB), whereas the control mice (C) received a sham injection. The food consisted of 51% galacto-oligosaccharides (GOS) and fructo-polysaccharides (9:1), 19% maltodextrin, 16% lactose and 14% glucose in experiment 1. In experiment 2, the FOS was replaced by additional GOS. GOS spray-dried powder of trans-galacto-oligosaccharides having a degree of polymerisation (dp) 3-8 (Vivinal G O S, Borculo Domo, Zwolle, N L) and FOS had a high degree of polymerisation (Raftiline H P, Orafti, Wijchen, N L; average dp>23). Following inoculation of tumour cells, tumour mass and skeletal muscles (extensor digitorum longus (EDL) and soleus muscles) were dissected and weighed.

Experiment 1
Control mice=C
Tumour-bearing mice=TB
Tumour-bearing+GOS/FOS=TB-Gos Fos
Experiment 2
Control mice=C
Tumour-bearing mice=TB
Tumour-bearing+GOS=TB-Gos
Results The table below represents the muscular mass (mg, +% loss to C) of experiments 1 and 2.

|  | m. EDL | m. Soleus |
| --- | --- | --- |
| Experiment 1 | | |
| C | 9.5 ± 0.8* | 6.5 ± 0.6* |
| TB | 7.7 ± 0.6 (−19.0%) | 5.5 ± 0.7 (−15.4%) |
| TB-Gos Fos | 8.2 ± 0.6 (−13.7%)* | 5.8 ± 0.9 (−10.6%) |
| Reduction in mass loss by Gos/Fos | 28% | 30% |
| Experiment 2 | | |
| C | 9.8 ± 0.8* | 7.5 ± 0.7* |
| TB | 7.7 ± 0.6 (−21.4%) | 5.6 ± 0.4 (−25.3%) |
| TB-Gos | 8.2 ± 0.6 (−16.3%)* | 6.2 ± 0.6 (−17.3%)* |
| Reduction in mass loss by Gos/Fos | 26% | 32% |

From the present data is concluded that galacto-oligosaccharides are responsible for the attenuation of the muscular loss in cancer cachexia. The asterisks (*) show statistical difference ($P<0.025$) with TB group.

EXAMPLE 2

A liquid formula was prepared for patients that suffer from chronic muscle wasting. It contains per 100 ml

| Energy | 658 kJ (157 kcal) |
| --- | --- |
| Protein [8.2 g casein and whey, 1.8 g Leu] | 10.0 g |
| Lipids [marine oil, vegetable] | 5.3 g |
| a. EPA | 0.56 g |
| b. DHA | 0.27 g |
| Carbohydrates | 17.4 g |
| a. sucrose | 4.21 g |
| b. maltodextrin | 8.42 g |
| c. trehalose | 4.21 g |
| d. lactose | 0.59 g |
| Fibre | 2.05 g |
| a. inulin DP>20 | 0.1 g |
| b. hydrolysed inulin DP<20 | 0.08 g |
| c. GOS | 1.53 g |
| d. resistant starch | 0.05 g |
| e. cellulose | 0.31 g |

EXAMPLE 3

A liquid formula was prepared for patients suffering from chronic muscle wasting. The formula contains per 100 ml:

| Energy | 662 kJ (158 kcal) |
| --- | --- |
| Protein [casein, whey + 1 g Leu, 0.5 g Met, 0.5 g Arg] | 10.0 g |
| Lipids [marine oil, vegetable] | 5.3 g |
| Carbohydrates [saccharide blend] | 17.5 g |
| Fibre [GOS + polyfructose 9:1] | 2.1 g |
| Ash | 1.2 g |

EXAMPLE 4

A liquid formula was prepared for patients suffering from chronic muscle wasting. The formula contains per 100 ml:

| Energy | 587 kJ (140 kcal) |
| --- | --- |
| Protein [casein + 0.9 g Leu, 0.5 g Ile, 0.2 g Val] | 9 g |
| Lipids | 5.0 g |
| Carbohydrates (10 wt. % free ribose) | 15 g |
| Fibre [hydrolysed guar + GOS ratio 3:7] | 1.5 g |
| Minerals/trace elements/vitamins including 60 μg folate | 2.0 g |

EXAMPLE 5

A liquid formula for patients suffering from chronic muscle wasting contains per 100 ml:

| Protein [casein 6.1 + whey 2.9 + free Leu 1.1] | 10.1 g |
| --- | --- |
| Lipids [EPA 0.6, DHA 0.29, ω-3/ω-6 = 1.16, PUFA's 2.5; MUFA 1.5; saturated 0.76] | 5.6 g |
| Digestible carbohydrates [sucrose 3.92, lactose 0.7 maltodextrins 7.84; trehalose 3.92] | 16.4 g |
| Fibre [hydrolysed inulin DP <20 0.2 + GOS 1.8] | 2.0 g |
| Minerals/trace elements/vitamins | |

The invention claimed is:

1. A method for the treatment of muscle wasting and/or chronic muscle wasting and/or sarcopenia, the method comprising administering to a patient suffering from muscle wasting, chronic muscle wasting and/or sarcopenia a nutritional composition comprising dietary fibre, wherein the dietary fiber comprises at least 30 wt. % of galactooligosaccharides having a chain length of 3-10 anhydromonose units and having a majority of anhydropyranose units.

2. The method according to claim 1, wherein the anhydropyranose units are selected from the group of galactose, mannose, xylose, their deoxy forms, amino forms and N-acylamino forms.

3. The method according to claim 1, wherein the dietary fibre comprises 30-96 wt. % of oligosaccharides in which the anhydromonose units have a majority of anhydro-galactose units and 4-50 wt. % of oligosaccharides and/or polysaccharides in which the anhydro-monose units have a majority of anhydrofructose units.

4. The method according to claim 1, wherein the dietary fibre comprises 50 to 100 wt % of the oligosaccharides having a chain length of 3-10 anhydromonose units.

5. The method according to claim 4, wherein the dietary fibre comprises 70 to 98 wt. % of the oligosaccharides having a chain length of 3-10 anhydromonose units.

6. The method according to claim 1, wherein the muscle wasting is associated with surgery, a trauma or inflammation.

7. The method according to claim 1, wherein the nutritional composition further comprises digestible carbohydrates, fats, proteins or a combination thereof.

8. The method according to claim 7, wherein the nutritional composition further comprises digestible carbohydrates, and the digestible carbohydrates comprise 20-80 wt. % of low-glycemic index and/or low-sweetness sugars selected from galactose, mannose, lactose, trehalose, palatinose and isomalto-oligosaccharides.

9. The method according to claim 1, wherein the nutritional composition is a liquid composition having a viscosity of less than 35 Mpa·s at a shear rate of 100 sec$^{-1}$ at 20° C.

10. The method according to claim 1, wherein the nutritional composition has an energy density between 5.0 and 16.8 kJ/ml (1.2 and 4.0 kcal/ml).

11. The method according to claim 1, wherein the nutritional composition has an energy density between 5.4 and 8.4 KJ/ml (1.3 and 2.0 kcal/ml).

12. The method according to claim 1, wherein the composition further comprises a component supporting nucleotide synthesis and folate metabolism.

13. The method according to claim 12, wherein the component supporting nucleotide synthesis and folate metabolism is folate in an amount of 50-1000 μg per g of fibre composition.

14. The method according to claim 1, wherein the composition further comprises a carbohydrate fraction having a glycemic index of less than 70% the glycemic index of glucose.

15. The method according to claim 1, comprising administering to a patient suffering from sarcopenia the nutritional composition.

16. The method according to claim 1, wherein the dietary fiber further comprises fructopolysaccharides or inulin.

17. The method according to claim 7, wherein the composition comprises 48-70 wt % essential amino acids.

\* \* \* \* \*